United States Patent
Piromchart et al.

(10) Patent No.: US 11,938,468 B2
(45) Date of Patent: Mar. 26, 2024

(54) CATALYST SYSTEM FOR PRODUCING CYCLIC CARBONATES AND METHOD RELATED THERETO

(71) Applicant: PTT EXPLORATION AND PRODUCTION PUBLIC COMPANY LIMITED, Bangkok (TH)

(72) Inventors: Taradon Piromchart, Bangkok (TH); Valerio D'Elia, Rayong (TH)

(73) Assignee: PTT EXPLORATION AND PRODUCTION PUBLIC COMPANY LIMITED, Bangkok (TH)

( * ) Notice: Subject to any disclaimer, the term of this patent is extended or adjusted under 35 U.S.C. 154(b) by 345 days.

(21) Appl. No.: 17/206,080

(22) Filed: Mar. 18, 2021

(65) Prior Publication Data

US 2021/0346877 A1    Nov. 11, 2021

Related U.S. Application Data

(63) Continuation of application No. PCT/TH2019/000042, filed on Sep. 18, 2019.

(60) Provisional application No. 62/732,987, filed on Sep. 18, 2018.

(51) Int. Cl.
| | | |
|---|---|---|
| *B01J 31/02* | (2006.01) | |
| *B01J 21/08* | (2006.01) | |
| *B01J 23/18* | (2006.01) | |
| *B01J 31/12* | (2006.01) | |
| *B01J 35/12* | (2006.01) | |
| *B01J 37/04* | (2006.01) | |
| *B01J 37/08* | (2006.01) | |
| *C07F 7/18* | (2006.01) | |
| *C07D 317/36* | (2006.01) | |

(52) U.S. Cl.
CPC ........... *B01J 31/0268* (2013.01); *B01J 21/08* (2013.01); *B01J 23/18* (2013.01); *B01J 31/0239* (2013.01); *B01J 31/0279* (2013.01); *B01J 31/0298* (2013.01); *B01J 31/121* (2013.01); *B01J 35/12* (2013.01); *B01J 37/04* (2013.01); *B01J 37/08* (2013.01); *C07F 7/1804* (2013.01); *C07D 317/36* (2013.01)

(58) Field of Classification Search
CPC ........ B01J 31/0268; B01J 21/08; B01J 23/18; B01J 31/0239; B01J 31/0279; B01J 31/0298; B01J 31/121; B01J 35/12; B01J 37/04; B01J 37/08; C07F 7/1804
See application file for complete search history.

(56) References Cited

U.S. PATENT DOCUMENTS

| | | | |
|---|---|---|---|
| 2015/0119584 A1* | 4/2015 | Yeh | B01J 31/2239 549/229 |
| 2016/0145234 A1* | 5/2016 | Takahashi | B01J 31/0269 549/230 |

OTHER PUBLICATIONS

Aquino et al., RSC Advances, (2015), 5(79), p. 64220-64227.*
International Search Report and Written Opinion dated Mar. 6, 2020 in connection with International Application No. PCT/TH2019/000042, 10 pages.
A.S. Aquino et al.: "Rationalizing the role of the anion in $CO_2$ capture and conversion using imidazolium-based ionic liquid modified mesoporous silica", RSC Advances, vol. 5, No. 79, Jul. 22, 2015, pp. 64220-64227.
Rafik Rajjak Shaikh et al.: "Catalytic Strategies for the Cycloaddition of Pure, Diluted, and Waste $CO_2$ to Epoxides under Ambient Conditions", ACS Catalysis, vol. 8, No. 1, Jan. 5, 2018, 32 pages.

* cited by examiner

*Primary Examiner* — Yong L Chu
(74) *Attorney, Agent, or Firm* — Baker & McKenzie LLP

(57) ABSTRACT

The present invention provides a catalyst system for producing cyclic carbonates comprising:
- a pre-catalyst, which is $BiCl_3$ having amounts in the range from 5 to 10% by weight of silica support;
- a compound having formula (I)

$$(I)$$

[chemical structure with $H_3CO$, $Si$, $OCH_3$, $R^1$, $R^2$, $R^3$, $N^+$, $Y^-$]

wherein:
Y is selected from bromide ($Br^-$) or iodide ($I^-$);
$R^1$, $R^2$, and $R^3$ are methyl group or $R^1$, $R^2$, and $R^3$ are taken together to form a heteroaryl ring having formula (II)

$$(II)$$

[imidazolium ring structure with $CH_3$]

and
a silica ($SiO_2$) support.

19 Claims, 4 Drawing Sheets

CATALYST SYSTEM FOR PRODUCING CYCLIC CARBONATES AND METHOD RELATED THERETO

CROSS-REFERENCE TO RELATED APPLICATIONS

This application is a continuation of and claims priority to International Application No. PCT/TH2019/000042, filed on Sep. 18, 2019, titled "Catalyst System for Producing Cyclic Carbonates and Method Related Thereto," which claims priority to U.S. Provisional Application No. 62/732,987 filed on Sep. 18, 2018, all of which are incorporated by reference in their entirety for all purposes.

FIELD OF INVENTION

This invention relates to a catalyst system for producing cyclic carbonates, and a method for preparation of the cyclic carbonates by using the catalyst system.

BACKGROUND OF INVENTION

Carbon dioxide ($CO_2$) emissions, such as from industrial processes and fuel combustion, are becoming a serious problem worldwide because such emissions are considered a primary driver of climate change. According to the Global Energy & $CO_2$ Status Report 2017 launched by the International Energy Agency (IEA), global energy-related $CO_2$ emissions reached a historic high of 32.5 gigatonnes. Legislators around the globe have started to set limitations on the unrestricted release of $CO_2$ in the atmosphere. Among approaches to solve the problem, the chemical transformation of $CO_2$ into high value chemicals has attracted considerable attention in recent years. Cyclic carbonates are one of those because they can be easily produced from the cycloaddition of $CO_2$ to epoxides under mild conditions. Cyclic carbonates are at the center of a multibillion USD market that involves polycarbonates, glycols, and polyesters. However, $CO_2$ is kinetically and thermodynamically stable, thus it requires a large amount of energy to transform $CO_2$ into other chemicals, including cyclic carbonates. As such, a promising approach is to develop effective catalysts that allow for higher conversion of $CO_2$ at lower temperatures.

Cyclic carbonates are produced from $CO_2$ by cycloaddition reaction to epoxides. Several catalyst systems exist to carry out such reaction, however, very few of such systems are capable of operating using impure $CO_2$ under ambient or moderate pressure (0.1 to 1 MPa). The ability to capture $CO_2$ from gas mixtures is advantageous as it can be easily applied with flue gas and is therefore commercially attractive for cyclic carbonate production. Examples of said catalysts include a bimetallic aluminum (salen) complex disclosed in Energy Environ. Sci., 2010, 3, 212-215 which is used for cyclic carbonate production with $CO_2$ having moisture and NOx as impurities in $CO_2$. However, said complex has a very high molecular weight and its preparation involves several synthetic steps because of the elaborated structure of organic framework-coordinating aluminum atoms.

U.S. Pat. No. 9,586,926 B2 disclosed a method for producing cyclic carbonate from carbonation of epoxide by $CO_2$. The method is performed via a homogeneous catalyst system comprising a pre-catalyst selected from $YCl_3$, $Y_2O_3$, $Y(NO_3)_3$, $ScCl_2$, or $LaCl_3$ and a co-catalyst selected from tetrabutylammonium bromide, 4-dimethylaminopyridine, or bis(triphenylphosphine) iminium chloride at a mole ratio in the range of 1:1 to 1:2. However, the catalytic activity of this system with impure or diluted $CO_2$ is relatively low under ambient conditions.

Monteiro, et. al. (Applied Catalysis A: General (2017), 544 (25), 46-54) disclosed a catalyst system comprising 1-methyl-3-(3-trimethoxysilylpropyl) imidazolium chloride ionic liquid catalyst supported on titanate nanotubes (TNT) or nanowires (TNW) as a pre-catalyst and $ZnBr_2$ as a co-catalyst for synthesizing cyclic carbonates. Although selectivity of the catalyst to $CO_2$ is high, this catalyst was not applied for the conversion of impure or diluted $CO_2$.

Therefore, there is a need to develop a new generation of catalytic systems to produce cyclic carbonates from $CO_2$, especially by using diluted and/or impure $CO_2$ sources, under mild conditions with high catalytic activity and high selectivity. Accordingly, the present invention is intended to provide a catalyst system for the conversion of $CO_2$ and epoxides to cyclic carbonates under mild conditions using pure and impure $CO_2$ having a high catalytic activity and being cost-effective.

SUMMARY OF THE INVENTION

In one embodiment, the present invention provides a catalyst system for producing cyclic carbonates from carbon dioxide ($CO_2$) and epoxide-based compounds comprising: a pre-catalyst, which is $BiCl_3$ having amounts in the range from 5 to 10% by weight of silica support;

a compound having the formula (I)

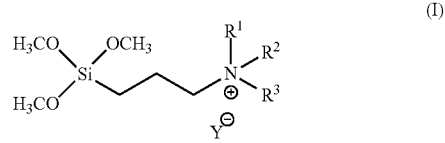

wherein:

Y is selected from bromide (Br⁻) or iodide (I⁻);

$R^1$, $R^2$, and $R^3$ are methyl group or $R^1$, $R^2$, and $R^3$ are taken together to form a heteroaryl ring having formula (II)

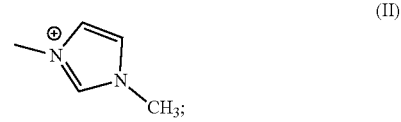

and a silica ($SiO_2$) support.

In another embodiment of the invention, the present invention relates to a method for preparation of a catalyst system of this invention comprising steps of:

(a) refluxing silane compound having the formula (III) with N-methylimidazole in an organic solvent at a temperature in the range of about 100 to 150° C. for about 12 to 72 hours, wherein a mole ratio between silane compound and N-methylimidazole is in the range of about 5:1 to about 1:5 to obtain compound (I) according to the present invention;

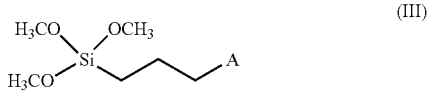

wherein:

A is selected from bromide (Br⁻) or iodide (I⁻);

(b) refluxing the mixture of the compound (I) obtained from step (a) and silica ($SiO_2$) support in an organic solvent at a temperature in the range of about 100 to 200° C. for about 5 to 50 hours, wherein the concentration of compound (I) is in the range of about 5 to 15% v/v and the concentration of silica ($SiO_2$) support is in the range of about 10 to 20% w/v; and (c) contacting $BiCl_3$ with the silica support obtained from step (b) for about 1 to 5 hours, wherein a concentration of $BiCl_3$ is in the range of about 5 to about 10% by weight of the silica support.

In another embodiment of the invention, the present invention relates to a method for preparation of a catalyst system of this invention comprising steps of:

(a) refluxing the mixture of N-3-(3-trimethoxysilylpropyl)-3-dimethylamine and silica ($SiO_2$) support in an organic solvent at a temperature in the range of about 100 to 200° C. for about 5 to 50 hours, wherein the concentration of N-3-(3-trimethoxysilylpropyl)-3-dimethylamine is in the range of about 5 to 15% v/v and the concentration of silica ($SiO_2$) support is in the range of about 10 to 20% w/v; and;

(b) mixing the product obtained from step (a) with an methyl iodide in an organic solvent at a temperature in the range of about 100 to 150° C. for about 12 to 72 hours, wherein the mole ratio between N-3-(3-trimethoxysilylpropyl)-3-dimethylamine and methyl iodide is in the range of about 5:1 to 1:5; and (c) contacting $BiCl_3$ with the silica support obtained from step (b) for about 1 to 5 hours, wherein the concentration of $BiCl_3$ is in the range of about 5 to 10% by weight of the silica support.

In another embodiment of the invention, the present invention relates to a method for producing cyclic carbonates, which comprises reacting epoxide-based compounds with carbon dioxide in the presence of a catalyst system comprising:

a pre-catalyst, which is $BiCl_3$ having amounts in the range from 5 to 10% by weight of silica support;

a compound having the formula (I)

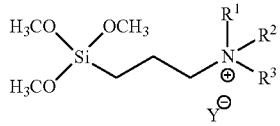

where:

X and Y is selected from bromide (Br⁻) or iodide (I⁻)

$R^1$, $R^2$, and $R^3$ are methyl group or $R^1$, $R^2$, and $R^3$ are taken together to form a heteroaryl ring having formula (II)

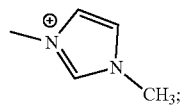

and a silica ($SiO_2$) support wherein said method is performed using the concentration of the catalyst system in the range of about 0.1 to 20 mol % relative to the epoxide-based compounds; at a pressure of carbon dioxide in the range of about 1 to 100 bar; a temperature in the range of about 10 to 200° C.; and a reaction time in the range of about 1 to 8 hours.

DETAILED DESCRIPTION OF THE INVENTION

Figure 1:
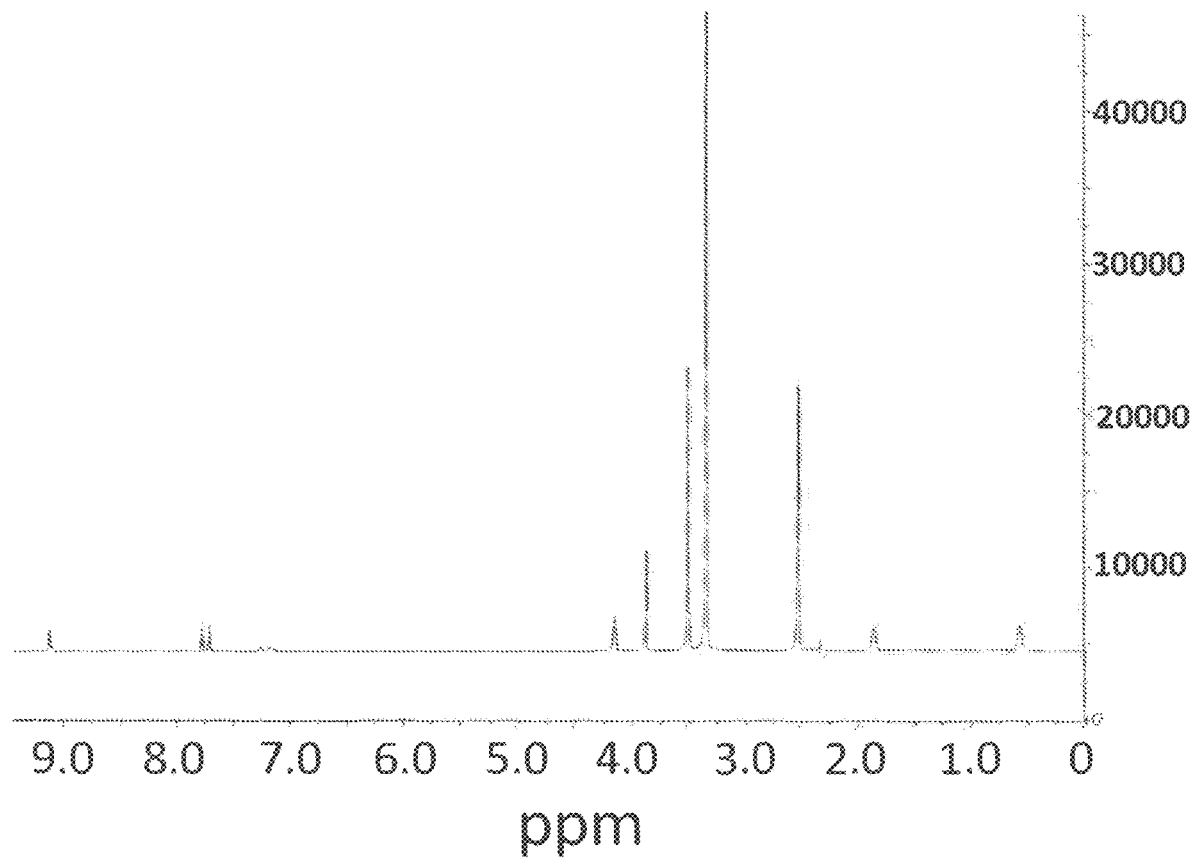
FIG. 1. ¹H-NMR spectrum of 1-methyl-3-(3-(trimethoxysilyl)propyl)-1H-imidazol-3-ium bromide.

The present invention provides a catalyst system for producing cyclic carbonates with cost-effectiveness and high catalytic activity for conversion of $CO_2$ and epoxide-based compounds to cyclic carbonates. Also, the present invention provides a method of making the cyclic carbonates by using the catalyst system with mild conditions using pure and impure $CO_2$. Details of the present invention can be elucidated according to the specification as follows.

Technical terms or scientific terms used herein have definitions as understood by those having an ordinary skill in the art, unless stated otherwise.

Equipment, apparatus, methods, or chemicals mentioned here means equipment, apparatus, processes, or chemicals commonly operated or used by those skilled in the art, unless explicitly stated otherwise that they are equipment, apparatus, methods, or chemicals specifically used in this invention.

The use of the singular or plural nouns with the term "comprising" in the claims or in the specification refers to "one" and also "one or more," "at least one," and "one or more than one."

All compositions and/or processes disclosed and claimed are aimed to include aspects of the invention from actions, operation, modifications, or changing of any parameters without performing significantly different experiments from this invention, and obtaining similar objects with the same utilities and results of the present invention according to persons skilled in the art although without mention of the claims specifically. Therefore, substitution or similar objects to the present invention including minor modifications or changes which can be clearly seen by persons skilled in the art should be considered within the scope, spirit, and concept of the invention as appended claims.

Throughout this application, the term "about" is used to indicate that any value presented herein may potentially vary or deviate. Such variation or deviation may result from errors of apparatus, methods used in calculation, or from individual operator implementing apparatus or methods. These include variations or deviations caused by changes of the physical properties.

Following is a detailed description of the invention without any intention to limit the scope of the invention.

According to one embodiment of the invention, the present invention provides a catalyst system for producing cyclic carbonates comprising:

a pre-catalyst, which is $BiCl_3$ having amounts in the range from 5 to 10% by weight of silica support;

a compound having the formula (I)

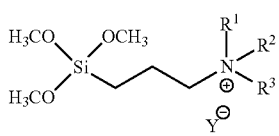

wherein:

Y is selected from bromide (Br⁻) or iodide (I⁻)

$R^1$, $R^2$, and $R^3$ are methyl group or $R^1$, $R^2$, and $R^3$ are taken together to form a heteroaryl ring having formula (II)

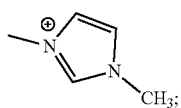

and a silica ($SiO_2$) support.

In another exemplary embodiment, Y is iodide (I⁻).

In a preferred exemplary embodiment, the compound having the formula (I) is selected from 1-methyl-3-(3-(trimethoxysilyl)propyl)-1H-imidazol-3-ium iodide or N,N,N-trimethyl-3-(trimethoxysilyl)propan-1-aminium iodide.

In another embodiment of the invention, this invention relates to a use of the catalyst system of the invention for producing cyclic carbonates from $CO_2$ and epoxide-based compounds.

In another embodiment of the invention, the present invention relates to a method for preparation of a catalyst system of this invention comprising steps of:

(a) refluxing silane compound having formula (III) with N-methylimidazole in an organic solvent at a temperature of 100 to 150° C. for 12 to 72 hours, wherein the mole ratio between the silane compound and N-methylimidazole is in the range of 5:1 to 1:5 to obtain compound (I) according to this invention;

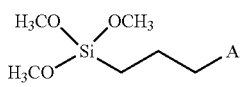

wherein:

A is selected from bromide (Br⁻) or iodide (I⁻);

(b) refluxing the mixture of the compound (I) obtained from step (a) and silica ($SiO_2$) support in an organic solvent at a temperature in the range of about 100 to 200° C. for about 5 to 50 hours, wherein the concentration of compound (I) is in the range of about 5 to 15% v/v and the concentration of silica ($SiO_2$) support is in the range of about 10 to 20% w/v; and (c) contacting $BiCl_3$ with the silica support obtained from step (b) for about 1 to 5 hours, wherein the concentration of $BiCl_3$ is in the range of about 5 to 10% by weight of the silica support.

In another exemplary embodiment, the mole ratio between the silane compound and N-methylimidazole is in the range of about 2:1 to 1:2.

In another exemplary embodiment, the organic solvent is an aromatic hydrocarbon solvent.

In a preferred exemplary embodiment, the organic solvent is toluene.

In one embodiment, according to step (c), contacting the pre-catalyst with the metal oxide obtained from step (b) may be performed by, for example, a dipping method, an impregnation method, a solid state reaction method, or the like, and among them, a solid state reaction method, such as grinding, mulling, or ball milling techniques is preferred because the operation is simple and offers excellent productivity.

In another embodiment of the invention, the present invention provides a method for preparation of a catalyst system according to the present invention comprising steps of:

(a) refluxing the mixture of N-3-(3-trimethoxysilylpropyl)-3-dimethylamine and silica ($SiO_2$) support in an organic solvent at a temperature in the range of about 100 to 200° C. for about 5 to 50 hours, wherein the concentration of N-3-(3-trimethoxysilylpropyl)-3-dimethylamine is in the range of about 5 to 15% v/v and the concentration of silica ($SiO_2$) support is in the range of about 10 to 20% w/v; and;

(b) mixing the product obtained from step (a) with an methyl iodide in an organic solvent at a temperature in the range of about 100 to 150° C. for about 12 to 72 hours, wherein the mole ratio between N-3-(3-trimethoxysilylpropyl)-3-dimethylamine and methyl iodide is in the range of about 5:1 to 1:5; and (c) contacting $BiCl_3$ with the silica support obtained from step (b) for about 1 to 5 hours, wherein the concentration of $BiCl_3$ is in the range of about 5 to 10% by weight of the silica support.

In another exemplary embodiment, wherein the organic solvent is selected from an aromatic hydrocarbon solvent.

In a preferred exemplary embodiment, the organic solvent is toluene.

In one embodiment, according to step (c), contacting the pre-catalyst with the metal oxide obtained from step (b) may be prepared by, for example, a dipping method, an impregnation method, a solid state reaction method, or the like, and among them, a solid state reaction method, such as grinding, mulling, or ball milling techniques is preferred because the operation is simple and offers excellent productivity.

In another embodiment of the invention, the present invention provides a method for producing cyclic carbonates from the reaction of carbon dioxide and epoxide-based compounds comprising reacting epoxide-based compounds with carbon dioxide in the presence of a catalyst system having:

a pre-catalyst, which is $BiCl_3$ having amounts in the range from 5 to 10% by weight of silica support;

a compound having the formula (I)

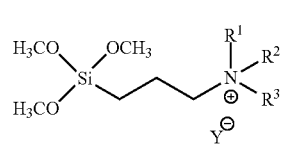

where:

Y is selected from bromide (Br⁻) or iodide (I⁻);

$R^1$, $R^2$, and $R^3$ are methyl group or $R^1$, $R^2$, and $R^3$ are taken together to form a heteroaryl ring having formula (II)

(II)

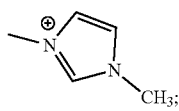

and
a silica (SiO$_2$) support
wherein said method is performed using a concentration of the catalyst system that is in the range of 0.1 to 20 mol % relative to the epoxide-based compounds; at a pressure of carbon dioxide in the range of 1 to 100 bar; a temperature in the range of 10 to 200° C.; and a reaction time in the range of 1 to 8 hours.

In a preferred exemplary embodiment, the concentration of the catalyst system is in the range of about 0.5 to 10 mol % relative to the epoxide-based compounds.

In a preferred exemplary embodiment, the pressure of carbon dioxide is in the range of about 1 to 10 bar.

In a preferred exemplary embodiment, the temperature is in the range of about 60 to 120° C.

In a preferred exemplary embodiment, the reaction time is in a range of about 2 to 4 hours.

In another exemplary embodiment, Y is iodide (I$^-$).

In a preferred exemplary embodiment, the compound having the formula (I) is selected from 1-methyl-3-(3-(trimethoxysilyl)propyl)-1H-imidazol-3-ium iodide or N,N,N-trimethyl-3-(trimethoxysilyl)propan-1-aminium iodide.

Hereafter, examples of the invention are shown without any purpose to limit any scope of the invention.

Example

Chemicals and Consumables

All chemicals were purchased from commercial sources and used as received. Early transition metal halides were stored and handled inside a glovebox. Metal-free compounds were stored in chemical cabinets and used without further precautions. Silica supports used for the preparation of the heterogeneous bismuth catalyst were thermally treated at about 150° C. in an oven before use to remove traces of moisture. Pure and diluted CO$_2$ (CO$_2$ at a concentration of 50% in air) were received in metal cylinders and dosed via regulator.

Synthesis of 1-methyl-3-(3-(trimethoxysilyl)propyl)-1H-imidazol-3-ium bromide

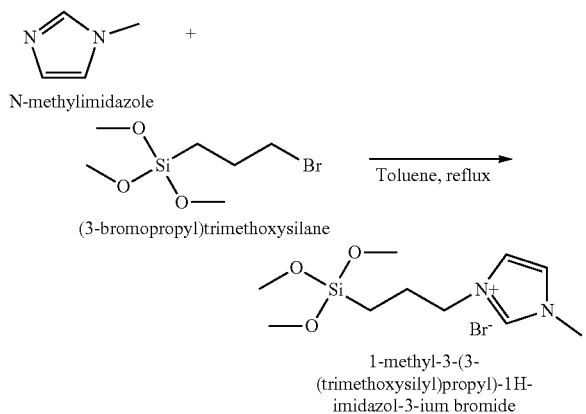

The mixture of N-Methylimidazole (about 5 mL) and (3-bromopropyl) trimethoxysilane (about 11.65 mL) in dry toluene was refluxed for about 48 hours in an inert atmosphere. The obtained mixture was washed with diethyl ether several times, and dried under a vacuum for about 24 hours. The resulting N-3-(3-trimethoxysilylpropyl)-3-methyl imidazolium bromide was a brownish viscous liquid. The structure of the product was identified by $^1$H-NMR in DMSO-d6 as shown in FIG. 1.

Synthesis of 1-methyl-3-(3-(trimethoxysilyl)propyl)-1H-imidazol-3-ium iodide

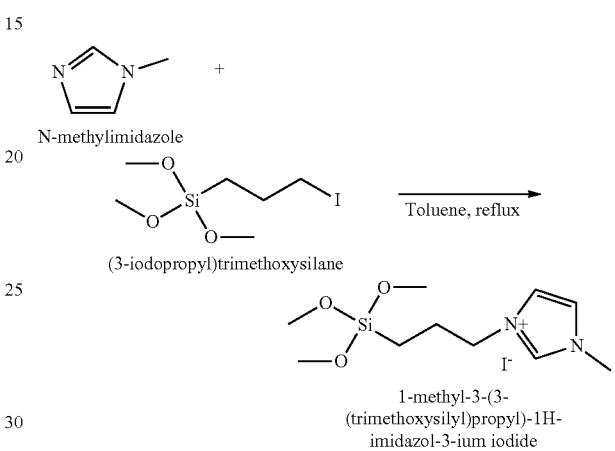

Figure 2:
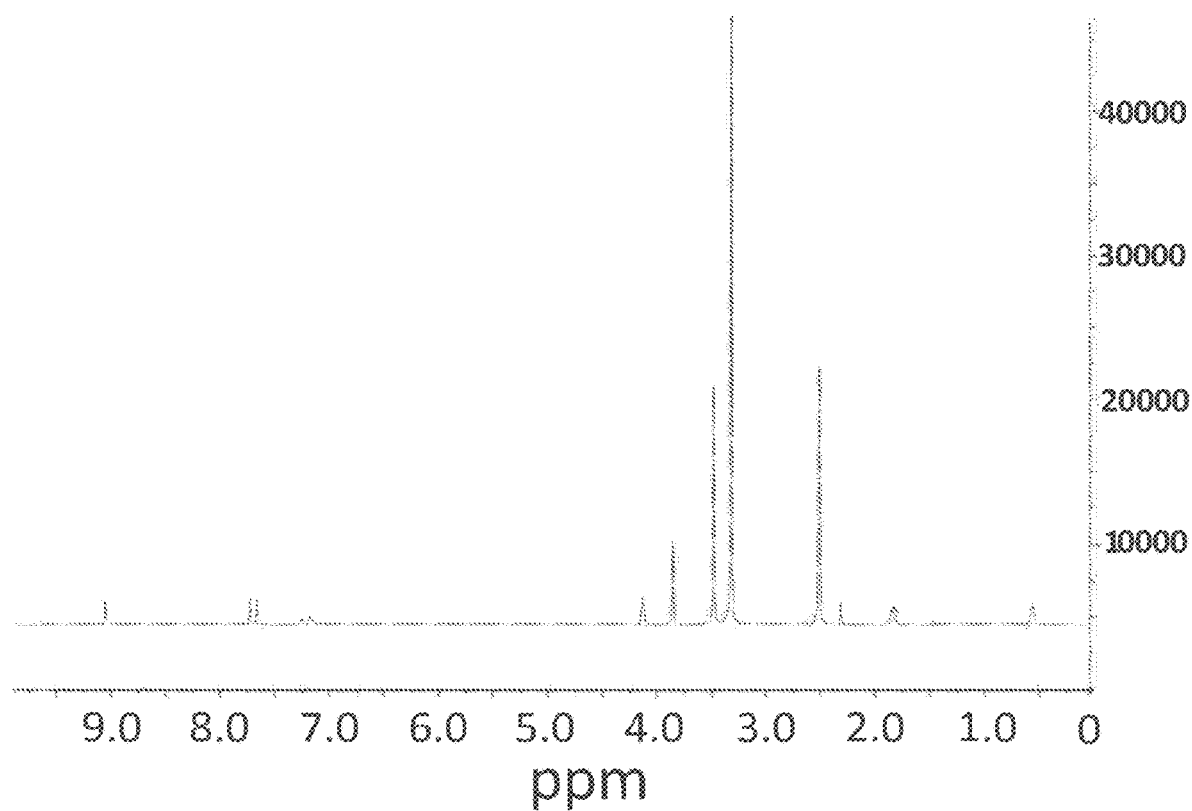
FIG. 2. ¹H-NMR spectrum of 1-methyl-3-(3-(trimethoxysilyl)propyl)-1H-imidazol-3-ium iodide.

A mixture of N-Methylimidazole (about 5 mL) and (3-iodopropyl) trimethoxysilane (about 11.65 mL) in dry toluene was refluxed for about 48 hours in an inert atmosphere. The obtained mixture was washed with diethyl ether several times, and dried under vacuum for about 24 hours. The resulting N-3-(3-trimethoxysilylpropyl)-3-methyl imidazolium iodide was a brown viscous liquid. The structure of the product was identified by $^1$H-NMR in DMSO-d6 as shown in FIG. 2.

Functionalization of SiO$_2$ with Ionic Liquid

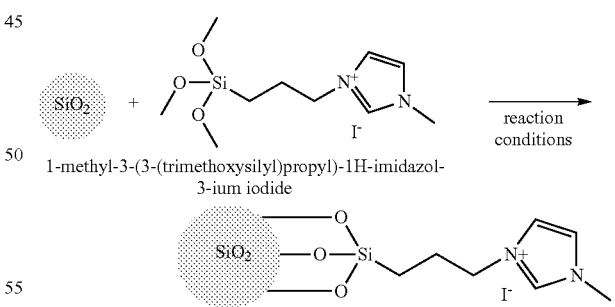

SiO$_2$ was functionalized with 1-methyl-3-(3-(trimethoxysilyl)propyl)-1H-imidazol-3-ium iodide. Silica (about 4 g) was suspended in toluene (about 25 mL.) N-3-(3-trimethoxysilylpropyl)-3-methyl imidazolium iodide (about 2.5 mL) dissolved in toluene was then added. After stirring the mixture for about 48 hours at about 110° C., the silica was allowed to settle down. The supernatant solution was separated by centrifugation and the modified silica was washed with toluene several times prior to being dried for about 24 hours in vacuum.

Figure 3:
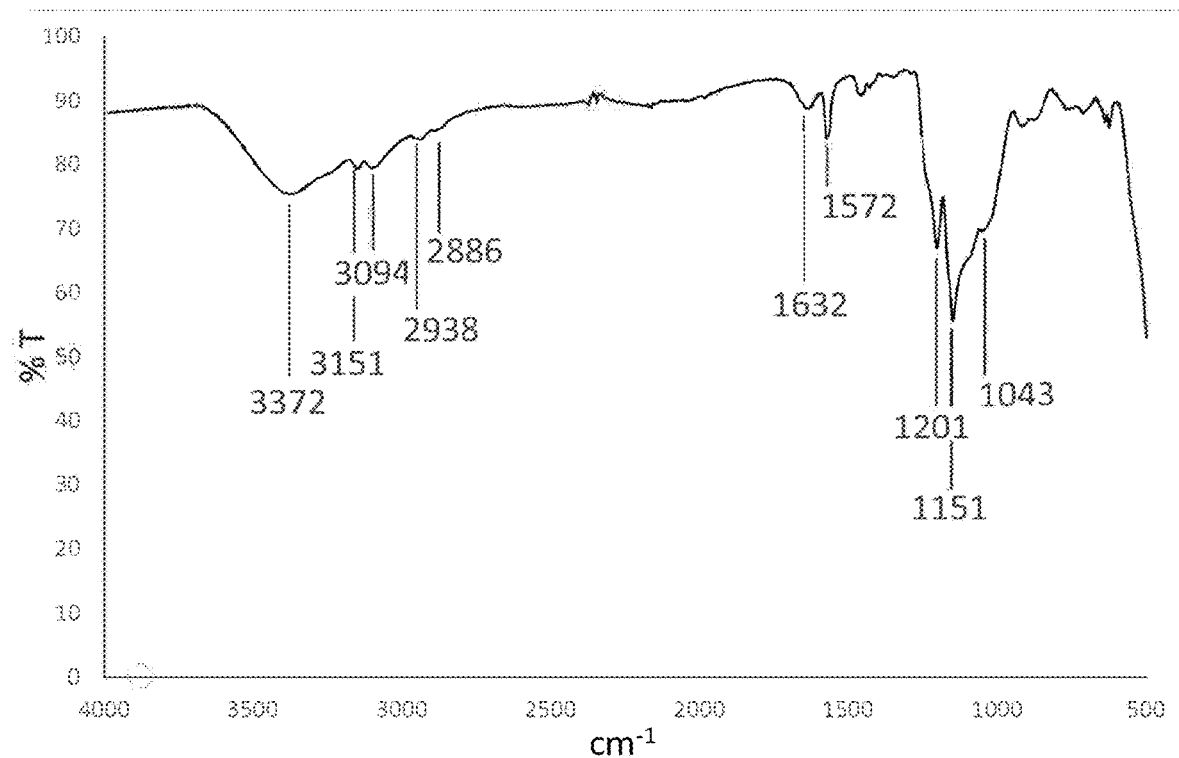
FIG. 3. FT-IR spectrum of 1-methyl-3-(3-(trimethoxysilyl)propyl)-1H-imidazol-3-ium iodide supported on SiO2.

The FT-IR spectrum of the prepared catalyst (FIG. 3) showed several signals corresponding to the presence of organic species with aromatic character on the surface as seen from the signals in the 2890 to 3151 cm$^{-1}$ region and in the 1450 to 1630 cm$^{-1}$ region. The presence of organic species loaded on the support was identified by the following elemental analysis: C (14.05%); H (2.65%); N (3.83%).

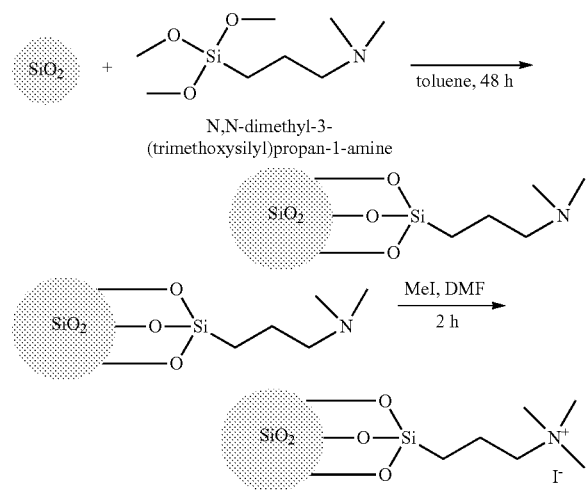

Additionally, SiO$_2$ was functionalized with N,N,N-trimethyl-3-(trimethoxysilyl)propan-1-aminium iodide followed by quaternarization of the amine with methyl iodide. SiO$_2$ (about 4 g) was suspended in toluene (about 25 mL). N-3-(3-trimethoxysilylpropyl)-3-dimethylamine (about 2.5 mL) dissolved in toluene was then added. After stirring the mixture for about 48 hours at about 110° C., the silica was allowed to settle down. The supernatant solution was separated by centrifugation and the modified silica was washed with toluene several times prior to being dried for about 24 hours in a vacuum. The resultant functionalized silica was further reacted with methyl iodide in DMF in the dark for about 2 hours to obtain quaternary ammonium salt. This step was repeated twice to ensure the formation of quaternarized amine. The supernatant solution was separated by centrifugation and the modified silica was washed with toluene several times prior to being dried for about 24 hours in vacuum.

Pre-Catalyst Loading on the Modified SiO$_2$

The loading of the pre-catalyst was carried out in the glove box. About 5 wt % and 10 wt % of metal of pre-catalyst with respect to the weight of silica was loaded on the functionalized supports. BiCl$_3$, as a pre-catalyst, was ground with the support through a manual mechanical grinding process. The mixture of modified silica support and pre-catalyst was ground for about 2 hours in the glove box and used as such.

Synthesis of Cyclic Carbonates Using Autoclave with Pure and Diluted CO$_2$

Cyclic carbonates were synthesized using the catalysts of the present invention to test their catalytic activity. The synthesis was carried out in a 75 mL autoclave under inert atmosphere (glove box). The catalysts of the present invention (about 0.5 to 1 g) and propylene oxide (about 5 mL, 71.4 mmol) were added to the autoclave equipped with a magnetic stir bar. The reactions were initialized with addition of 10 bar CO$_2$ (CO$_2$ at a concentration of about 50% and about 100% were used). The autoclave was set in an oil-bath at about 60° C. and about 80° C. and stirred at about 500 rpm. After about 3 hours, the vessel was allowed to cool to room temperature in a water bath. The crude reaction mixture sample was collected for $^1$H NMR.

Figure 4:
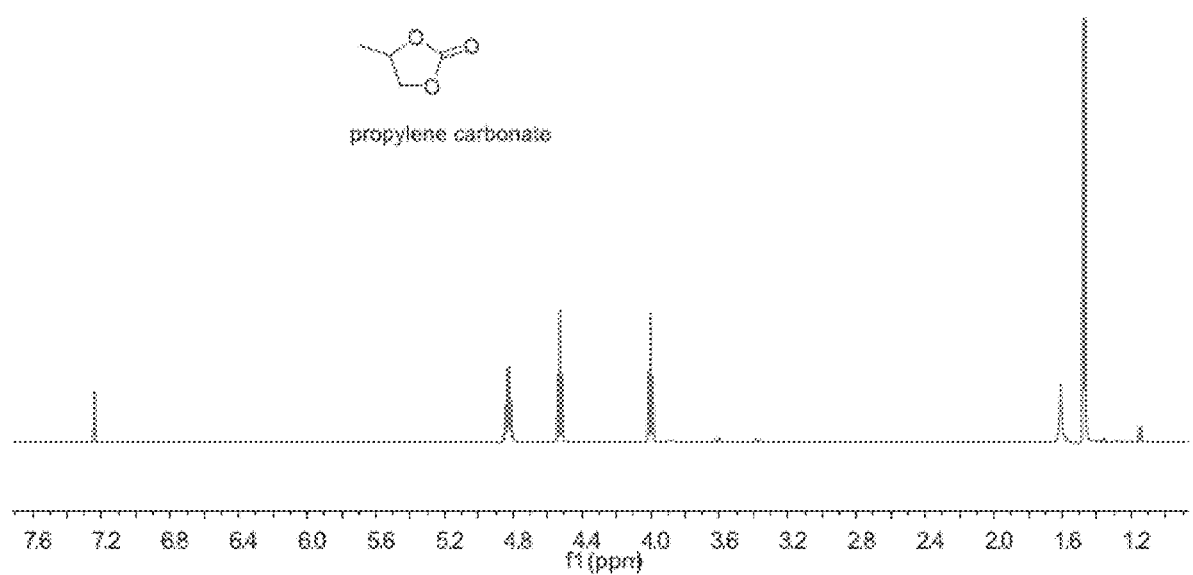
FIG. 4. ¹H-NMR spectrum of propylene carbonate obtained from the catalyst according to the present invention.

For isolation of pure propylene carbonate, the reaction mixture was filtered, and unreacted propylene oxide was evaporated by a rotary evaporator. The propylene carbonate obtained from the reaction was identified by $^1$H-NMR in CDCl$_3$ (FIG. 4).

From Table 1, the initial studies on heterogeneous catalysts were carried out at about 60 and 80° C. and 10 bar CO$_2$ pressure using either pure CO$_2$ or diluted CO$_2$ at a concentration of about 50%. The studied catalysts were N,N,N-trimethyl-3-(trimethoxysilyl)propan-1-aminium iodide and BiCl$_3$ supported on SiO$_2$ (SiNMe$_2$-MeI—BiCl$_3$), and 1-methyl-3-(3-(trimethoxysilyl)propyl)-1H-imidazol-3-ium iodide and BiCl$_3$ supported on SiO$_2$ (Si-ImI-BiCl$_3$). Before running catalytic activity tests with the metal containing catalysts, the catalytic efficiency of the metal-free functionalized supports (entries 1 to 4) were studied. Of note, the metal-free functionalized supports showed a moderate to good catalytic activity in the cycloaddition of CO$_2$ to propylene oxide. However, this catalytic activity in all entries was improved by the presence of BiCl$_3$. The catalytic activity in the presence of metal was improved about 10 to 20% compared to the absence of metal. A comparison between entries 5 and 6 suggested that the metal loading could be reduced to about 5% by weight without a minimal difference in catalytic activity. The reaction condition at about 80° C. and about 10 bar using pure CO$_2$ with 10% metal loading of SiNMe$_2$-MeI—BiCl$_3$ (entry 9) provided the highest reaction yields with a completion of CO$_2$ conversion in about 3 hours. Reducing the temperature to about 60° C., with pure or diluted CO$_2$ (concentration of about 50%) led to slightly lower conversion. Using the diluted CO$_2$ led to a decrease of the reaction yield when operating at about 80° C., however, at about 60° C., the yields of the reactions using pure CO$_2$ and the diluted CO$_2$ were similar. SiNMe$_2$-MeI—BiCl$_3$ was recovered after the catalytic run and reused for two additional consecutive cycles. The results showed that the catalyst was recyclable with a progressive loss of catalytic activity. This might probably be due to the exposition of the catalyst to air and/or to losses of material occurring when recycling the catalyst.

TABLE 1

Catalytic activity of the catalyst.

| Entry | Type of catalyst | Catalyst system | Pressure (bar)/ temperature (° C.) | CO$_2$ concentration (%) | % Conversion of CO$_2$ (at about 3 hours) |
|---|---|---|---|---|---|
| 1 | modified support | Si-ImI | 10/80 | 100 | 82 |
| 2 | without pre- | Si-ImI | 10/60 | 50 | 52 |
| 3 | catalyst loading | Si—Nme$_2$—MeI | 10/80 | 100 | 81 |

TABLE 1-continued

Catalytic activity of the catalyst.

| Entry | Type of catalyst | Catalyst system | Pressure (bar)/ temperature (° C.) | $CO_2$ concentration (%) | % Conversion of $CO_2$ (at about 3 hours) |
|---|---|---|---|---|---|
| 4 |  | Si—Nme$_2$—MeI | 10/60 | 50 | 74 |
| 5 | 5% wt. metal | Si-ImI-BiCl$_3$ | 10/80 | 100 | 90 |
| 6 | 10% wt. metal | Si-ImI-BiCl$_3$ | 10/80 | 100 | 92 |
| 7 |  | Si-ImI-BiCl$_3$ | 10/80 | 50 | 76 |
| 8 |  | Si-ImI-BiCl$_3$ | 10/60 | 50 | 76 |
| 9 |  | Si—Nme$_2$—MeI—BiCl$_3$ | 10/80 | 100 | 100 |
| 10 |  | Si—Nme$_2$—MeI—BiCl$_3$ | 10/80 | 50 | 78 |
| 11 |  | Si—Nme$_2$—MeI—BiCl$_3$ | 10/60 | 100 | 79 |
| 12 |  | Si—Nme$_2$—MeI—BiCl$_3$ | 10/60 | 50 | 79 |
| 13 | Recyclability | Si—Nme$_2$—MeI—BiCl$_3$ | 10/80 | 50 | 83 |
| 14 | study | Si—Nme$_2$—MeI—BiCl$_3$ (1st reuse) | 10/80 | 50 | 70 |
| 15 |  | Si—Nme$_2$—MeI—BiCl$_3$ (2nd reuse) | 10/80 | 50 | 62 |

According to the good catalytic activity of SiNMe$_2$-MeI—BiCl$_3$ and Si-ImI-BiCl$_3$, further studies and optimization by varying temperature and pressure using the diluted $CO_2$ (concentration of about 50%) were carried out as shown in Table 2.

The data in Table 2 showed that increasing the temperature from about 80° C. to about 120° C. for Si—NMe$_2$-MeI—BiCl$_3$ led to an increase of yield, however, the conversions of $CO_2$ between at about 80° C. and at about 100 to 120° C. were not much different. The pressure caused a small effect on the catalytic performance as the data in Table 2 showed that nearly complete conversion of C02 could be obtained even at about 5 bar C02 pressure. Table 4 (Entry 5) showed that at about 60° C. and about 7 bar $CO_2$ pressure were the mildest condition to achieve $CO_2$ conversion with a high yield (93%). When using Si-ImI-BiCl$_3$, the most interesting observation was that $CO_2$ conversion did not generally increase with the temperature, but generally decreased, especially when the temperature rose from about 100 to 120° C. This might be because the vaporization of propylene oxide while increasing temperature could reduce the contact between the substrate and the catalyst. This observation was supported by the fact that the conversion decreased when the temperature increased from about 100 to 120° C. at the $CO_2$ pressure of about 5 bar (Table 2, Entries 23 and 24), since this condition favored propylene oxide evaporation.

TABLE 2

Catalytic activity of the prepared catalyst system under several reaction conditions.

| Entry | Catalyst system | Pressure (bar)/ temperature (° C.) | $CO_2$ concentration (%) | % Conversion of $CO_2$ (at about 3 hours) |
|---|---|---|---|---|
| 1 | Si—Nme$_2$—MeI—BiCl$_3$ | 10/60 | 50 | 79 |
| 2 | Si—Nme$_2$—MeI—BiCl$_3$ | 10/80 | 50 | 83 |
| 3 | Si—Nme$_2$—MeI—BiCl$_3$ | 10/100 | 50 | 100 |
| 4 | Si—Nme$_2$—MeI—BiCl$_3$ | 10/120 | 50 | 100 |
| 5 | Si—Nme$_2$—MeI—BiCl$_3$ | 7/60 | 50 | 93 |
| 6 | Si—Nme$_2$—MeI—BiCl$_3$ | 7/80 | 50 | 93 |
| 7 | Si—Nme$_2$—MeI—BiCl$_3$ | 7/100 | 50 | 100 |
| 8 | Si—Nme$_2$—MeI—BiCl$_3$ | 7/120 | 50 | 100 |
| 9 | Si—Nme$_2$—MeI—BiCl$_3$ | 5/80 | 50 | 87 |
| 10 | Si—Nme$_2$—MeI—BiCl$_3$ | 5/80 | 50 | 87 |
| 11 | Si—Nme$_2$—MeI—BiCl$_3$ | 5/60 | 50 | 100 |
| 12 | Si—Nme$_2$—MeI—BiCl$_3$ | 5/60 | 50 | 100 |
| 13 | Si-ImI-BiCl$_3$ | 10/60 | 50 | 76 |
| 14 | Si-ImI-BiCl$_3$ | 10/80 | 50 | 100 |
| 15 | Si-ImI-BiCl$_3$ | 10/100 | 50 | 96 |
| 16 | Si-ImI-BiCl$_3$ | 10/120 | 50 | 100 |
| 17 | Si-ImI-BiCl$_3$ | 7/60 | 50 | 99 |
| 18 | Si-ImI-BiCl$_3$ | 7/80 | 50 | 93 |
| 19 | Si-ImI-BiCl$_3$ | 7/100 | 50 | 93 |
| 20 | Si-ImI-BiCl$_3$ | 7/120 | 50 | 68 |
| 21 | Si-ImI-BiCl$_3$ | 5/60 | 50 | 87 |
| 22 | Si-ImI-BiCl$_3$ | 5/80 | 50 | 96 |
| 23 | Si-ImI-BiCl$_3$ | 5/100 | 50 | 61 |
| 24 | Si-ImI-BiCl$_3$ | 5/120 | 50 | 35 |

As a person skilled in the art will readily appreciate, the above description is meant as an illustration of implementation of the principles this invention. This description is not intended to limit the scope or application of this invention in that the invention is susceptible to modification, variation, and change, without departing from the spirit of this invention, as defined in the following claims.

BEST MODE OF THE INVENTION

Best mode of the invention is as provided in the description of the invention.

The invention claimed is:

1. A catalyst system for producing cyclic carbonates comprising:
   a pre-catalyst, which is BiCl$_3$ having amounts in the range from 5 to 10% by weight of silica support;
   a compound having formula (I)

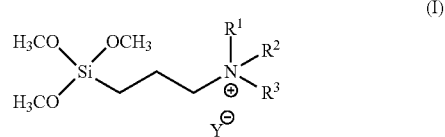

wherein:
   Y is selected from bromide (Br⁻) or iodide (I⁻);
   $R^1$, $R^2$, and $R^3$ are methyl group or $R^1$, $R^2$, and $R^3$ are taken together to form a heteroaryl ring having formula (II)

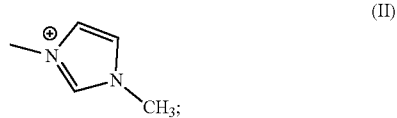

and
   a silica ($SiO_2$) support.

2. The catalyst system according to claim 1, wherein Y is iodide (I⁻).

3. The catalyst system according to claim 1, wherein the compound having formula (I) is selected from 1-methyl-3-(3-(trimethoxysilyl)propyl)-1H-imidazol-3-ium iodide or N,N,N-trimethyl-3-(trimethoxysilyl)propan-1-aminium iodide.

4. A method for preparation of a catalyst system for producing cyclic carbonates according to claim 1 comprising steps of:
   (a) refluxing a silane compound having formula (III) with N-methylimidazole in an organic solvent at a temperature of 100 to 150° C. for 12 to 72 hours, wherein the mole ratio between the silane compound and N-methylimidazole is in the range of 5:1 to 1:5 to obtain compound (I) according to claim 1;

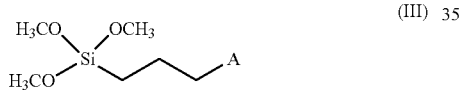

wherein:
   A is selected from bromide (Br⁻) or iodide (I⁻);
   (b) refluxing the mixture of the compound (I) obtained from step (a) and silica ($SiO_2$) support in an organic solvent at a temperature in the range of 100 to 200° C. for 5 to 50 hours, wherein the concentration of compound (I) is in the range of 5 to 15% v/v and the concentration of silica ($SiO_2$) support is in the range of 10 to 20% w/v; and
   (c) contacting $BiCl_3$ with the silica support obtained from step (b) for 1 to 5 hours, wherein the concentration of $BiCl_3$ is in the range of 5 to 10% by weight of the silica support.

5. The method according to claim 4, wherein the mole ratio between the silane compound and N-methylimidazole is in the range of 2:1 to 1:2.

6. The method according to claim 4, wherein the organic solvent is an aromatic hydrocarbon solvent.

7. The method according to claim 6 wherein the organic solvent is toluene.

8. The method according to claim 4, wherein step (c) is performed using a solid state reaction method.

9. A method for preparation of a catalyst system for producing cyclic carbonates according to claim 1 comprising steps of:
   (a) refluxing the mixture of N-3-(3-trimethoxysilylpropyl)-3-dimethylamine silica ($SiO_2$) support in an organic solvent at 100 to 200° C. for 5 to 50 hours, wherein the concentration of N-3-(3-trimethoxysilylpropyl)-3-dimethylamine is in the range of 5 to 15% v/v and the concentration of silica ($SiO_2$) support is in the range of 10 to 20% w/v; and;
   (b) mixing the product obtained from step (a) with an methyl iodide in an organic solvent at a temperature of 100 to 150° C. for 12 to 72 hours, wherein the mole ratio between N-3-(3-trimethoxysilylpropyl)-3-dimethylamine and methyl iodide is in the range of 5:1 to 1:5; and
   (c) contacting $BiCl_3$ with the silica support obtained from step (b) for 1 to 5 hours, wherein the concentration of $BiCl_3$ is in the range of 5 to 10% by weight of the silica support.

10. The method according to claim 9, wherein the organic solvent is selected from an aromatic hydrocarbon solvent.

11. The method according to claim 10 wherein the organic solvent is toluene.

12. The method according to claim 9, wherein step (c) is performed using a solid state reaction method.

13. A method for producing cyclic carbonates from the reaction of carbon dioxide and epoxide-based compounds which comprises reacting epoxide-based compounds with carbon dioxide in the presence of a catalyst system comprising:
   a pre-catalyst, which is $BiCl_3$ having amounts in the range from 5 to 10% by weight of silica support;
   a compound having formula (I)

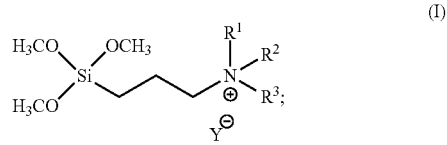

and
   a silica ($SiO_2$) support
   where:
   Y is selected from bromide (Br⁻) or iodide (I⁻);
   $R^1$, $R^2$, and $R^3$ are methyl group or $R^1$, $R^2$, and $R^3$ are taken together to form a heteroaryl ring having formula (II)

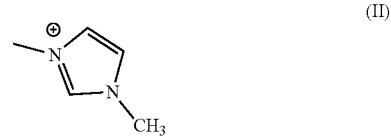

wherein said method is performed using a concentration of the catalyst system in the range of 0.1 to 20 mol% relative to the epoxide-based compounds; at a pressure of carbon dioxide in the range of 1 to 100 bar; a temperature in the range of 10 to 200° C.; and a reaction time in the range of 1-8 hours.

14. The method according to claim 13, wherein the concentration of the catalyst system is in the range of 0.5 to 10 mol % relative to the epoxide-based compounds.

15. The method according to claim 13, wherein the pressure of carbon dioxide is in the range of 1 to 10 bar.

16. The method according to claim 13, wherein the temperature is in the range of 60 to 120° C.

17. The method according to claim 13, wherein the reaction time is in the range of 2 to 4 hours.

18. The method according to claim 13, wherein Y is iodide (I⁻).

19. The method according to claim 13, wherein the compound having formula (I) is selected from 1-methyl-3-(3-(trimethoxysilyl)propyl)-1H-imidazol-3-ium iodide or N,N,N-trimethyl-3-(trimethoxysilyl)propan-1-aminium iodide.

* * * * *